(12) United States Patent
Garcia

(10) Patent No.: US 11,771,481 B2
(45) Date of Patent: Oct. 3, 2023

(54) STERNAL PLATES AND METHODS OF USE

(71) Applicant: Zimmer Biomet CMF and Thoracic, LLC, Jacksonville, FL (US)

(72) Inventor: Saddy Rodolfo Garcia, St. Augustine, FL (US)

(73) Assignee: Zimmer Biomet CMF and Thoracic, LLC, Jacksonville, FL (US)

(*) Notice: Subject to any disclaimer, the term of this patent is extended or adjusted under 35 U.S.C. 154(b) by 0 days.

(21) Appl. No.: 17/675,563

(22) Filed: Feb. 18, 2022

(65) Prior Publication Data

US 2022/0280213 A1 Sep. 8, 2022

Related U.S. Application Data

(60) Provisional application No. 63/158,227, filed on Mar. 8, 2021.

(51) Int. Cl.
*A61B 17/80* (2006.01)
*A61B 17/88* (2006.01)
(Continued)

(52) U.S. Cl.
CPC ........ *A61B 17/8076* (2013.01); *A61B 17/808* (2013.01); *A61B 17/8009* (2013.01);
(Continued)

(58) Field of Classification Search
CPC ............ A61B 17/8004; A61B 17/8019; A61B 17/8076; A61B 17/808; A61B 17/823;
(Continued)

(56) References Cited

U.S. PATENT DOCUMENTS

| | | | |
|---|---|---|---|
| 5,849,012 A | * | 12/1998 | Abboudi ............ A61B 17/8076 606/86 R |
| 6,007,538 A | | 12/1999 | Levin |

(Continued)

FOREIGN PATENT DOCUMENTS

| | | |
|---|---|---|
| CN | 106108995 A | 11/2016 |
| EP | 1365693 A1 | 12/2003 |

(Continued)

OTHER PUBLICATIONS

"European Application Serial No. 22160930.8, Extended European Search Report dated Aug. 10, 2022", 10 pgs.

(Continued)

*Primary Examiner* — Larry E Waggle, Jr.
(74) *Attorney, Agent, or Firm* — SCHWEGMAN LUNDBERG & WOESSNER, P.A.

(57) ABSTRACT

A plate system for securing a first sternal portion and a second sternal portion of a separated sternum can include a first plate and a second plate. The first plate can include a first body and a first hook. The first body can include a first reduction bore. The first hook can extend from the first body. The first hook can be engageable with a lateral portion of the first sternal portion. The second plate can include a second body and a second hook. The second body can include a second reduction bore. The second hook can extend from the second body. The second hook can be engageable with a lateral portion of the second sternal portion opposite the first hook.

17 Claims, 15 Drawing Sheets

(51) Int. Cl.
*A61B 17/82* (2006.01)
*A61B 17/84* (2006.01)

(52) U.S. Cl.
CPC ........ *A61B 17/8019* (2013.01); *A61B 17/823* (2013.01); *A61B 17/84* (2013.01); *A61B 17/88* (2013.01); *A61B 17/8866* (2013.01)

(58) Field of Classification Search
CPC .. A61B 17/88; A61B 17/8866; A61B 17/8872
See application file for complete search history.

(56) References Cited

U.S. PATENT DOCUMENTS

| | | | |
|---|---|---|---|
| 6,051,007 | A | 4/2000 | Hogendijk et al. |
| 6,200,318 | B1 | 3/2001 | Har-shai et al. |
| 6,872,210 | B2 | 3/2005 | Hearn |
| 7,229,444 | B2 | 6/2007 | Boyd |
| 7,731,718 | B2 | 6/2010 | Schwammberger et al. |
| 8,162,996 | B2 | 4/2012 | Schelling |
| 8,177,822 | B2 | 5/2012 | Medoff |
| 8,221,421 | B2 | 7/2012 | Hearn |
| 8,460,345 | B2 | 6/2013 | Steger et al. |
| 8,632,573 | B2 | 1/2014 | Ellis et al. |
| 8,876,824 | B2 | 11/2014 | Hearn |
| 8,961,574 | B2 | 2/2015 | Bluechel et al. |
| 9,237,910 | B2 | 1/2016 | Seykora et al. |
| 9,468,467 | B2 | 10/2016 | Rathbun et al. |
| 9,561,064 | B2 | 2/2017 | Goodwin et al. |
| 10,022,169 | B2 | 7/2018 | Waizenegger et al. |
| 10,206,719 | B2 | 2/2019 | Goel |
| 10,426,532 | B2 | 10/2019 | Goodwin et al. |
| 2008/0147125 | A1* | 6/2008 | Colleran ............ A61B 17/8004 606/280 |
| 2010/0179600 | A1 | 7/2010 | Steger et al. |
| 2018/0168699 | A1 | 6/2018 | Goel |
| 2019/0167315 | A1 | 6/2019 | Goel |
| 2019/0262040 | A1 | 8/2019 | Kono |
| 2019/0374267 | A1* | 12/2019 | Madey ................. A61B 17/823 |
| 2020/0337750 | A1 | 10/2020 | Hu et al. |

FOREIGN PATENT DOCUMENTS

| | | |
|---|---|---|
| EP | 1654994 A1 | 5/2006 |
| EP | 1654994 B1 | 4/2008 |
| EP | 2564797 A1 | 3/2013 |
| EP | 2708199 A1 | 3/2014 |
| EP | 2838458 A1 | 2/2015 |
| EP | 2708199 B1 | 11/2017 |
| EP | 2838458 B1 | 9/2018 |
| EP | 2564797 B1 | 10/2020 |

OTHER PUBLICATIONS

"European Application Serial No. 22160930.8, Response filed Mar. 14, 2023 to Extended European Search Report dated Aug. 10, 2022", 17 pgs.

* cited by examiner

STERNAL PLATES AND METHODS OF USE

CLAIM OF PRIORITY

This application claims the benefit of U.S. Provisional Patent Application Ser. No. 63/158,227, filed on Mar. 8, 2021, the benefit of priority of which is claimed hereby, and which is incorporated by reference herein in its entirety.

BACKGROUND

A sternotomy is a procedure performed to separate a sternum of a patient to gain access to the chest cavity of the patient, such as for corrective heart procedures. During a sternotomy procedure a vertical (superior to inferior) cut is made through the sternum allowing the sternum to be cracked or separated into two halves to provide access to the chest cavity. Following a procedure within the chest cavity, the sternum must be closed. Commonly, sternotomies are closed or repaired using one or more wire cerclages wrapped around the sternal halves. In some cases, at least one rigid bone plate is used to bridge and secure to the approximated sternal halves using bone screws.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
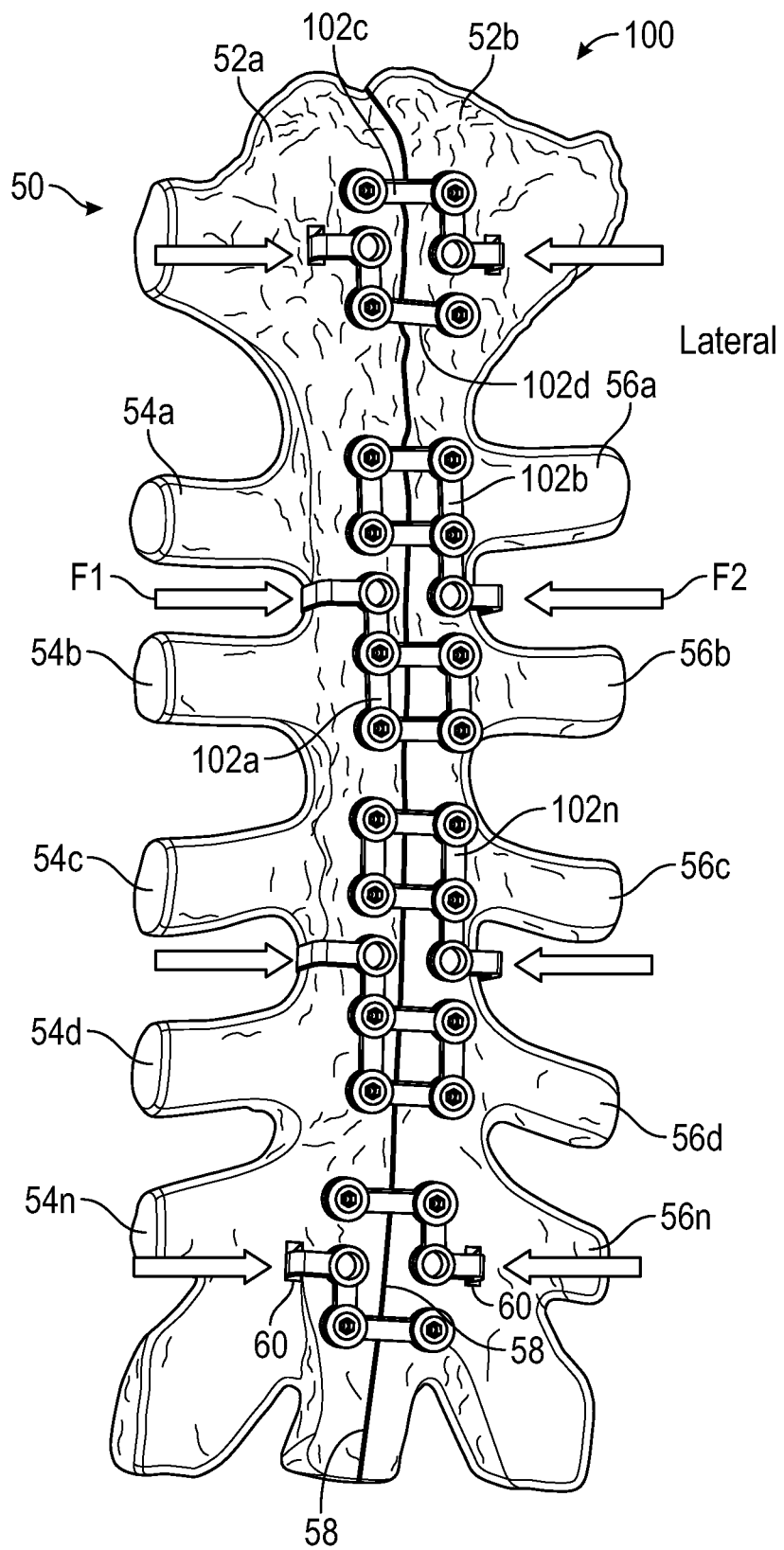
FIG. 1A illustrates an isometric view of a sternum, ribs, and plate assemblies.

Sternotomies are often performed on a sternum of a patient (such as prior to a cardiac procedure) by creating a midline resection and separating two halves or portions of the sternum for access to the chest cavity of the patient. Following the procedure, the sternum is often repaired using one or more wire cerclages to hold the sternal halves in place while the halves heal together. While wire cerclages can help to prevent medial-lateral separation (or relative movement of the halves) of the sternum, wire cerclages are sometimes ineffective at limiting relative anterior-posterior movement of the halves and at limiting relative superior-inferior movement of the halves. Wire cerclages can also unintentionally penetrate outer portions of the sternum. Rigid bone plates are a strategy often used to address the shortcomings of wire cerclages. Rigid bone plates can be secured to each portion or half of the sternum and can help to limit relative movement of the sternal halves in all directions. Nevertheless, it can be difficult to approximate and reduce the sternal halves using flat rigid bone plates in the same manner as wires.

This disclosure helps to address these issues by including a sternal plating system that includes features (such as hooks) built into the plates for approximating and/or reducing, and fixating the sternal halves (or two sections of bones). For example, a first sternal plate can include a hook for engaging a lateral portion (intercostal region) of a first sternal half and a second sternal plate can include a hook for engaging a lateral portion of a second sternal half. The sternal plates can be secured to a reduction tool and the hooks can be engaged with their respective sternal halves. The reduction tool can be used to approximate and reduce the sternal halves by applying forces to the hooks to deliver approximately equal and opposite forces on the sternal halves until the sternal halves contact each other.

Once the sternal halves are together, the sternal plates can receive fasteners therethrough to secure each plate to both halves of the sternum. Afterwards, the reduction tool is decoupled. This method of fixation with opposing plates with hooks helps to decrease the relative movement of the sternum in medial-lateral, anterior-posterior, and superior-inferior directions more than when using standard plates or wires. Combining wires and plates together to fixate the sternal halves can produce fixation similar to the opposing plates with hooks disclosed in the present application, but the hooks of the opposing plates of the present application can be more stable than a combination of wires and plates and are less likely to cut thru the bone than wires.

Furthermore, this fixation approach, implanting opposing plates simultaneously and while coupled to the aforementioned/disclosed reduction tool, is an improvement over wires and plates because the direct force transferred from the reduction tool through the hooks to the sternal haves firmly holds the sternal halves together during the insertion of the screws through each opposing plate at both sides of the sternotomy line.

To further explain this particular benefit through an example, if a reduction tool is first used to reduce the sternal halves and then plates without hooks are placed and fixated one at a time, the quality of the approximation between the two sternal halves could be compromised when the reduction tool is removed. This disclosure helps to address these issues by providing a method and apparatus for simultaneously reducing sternal halves together by using a reduction tool in combination with one or multiple pairs of opposing plates with hooks, and by fixating each single plate with screws at both sides of the sternotomy line while the force imparted through the hooks in each plate firmly holds the sternal halves together.

The above discussion is intended to provide an overview of the subject matter of the present patent application. It is not intended to provide an exclusive or exhaustive explanation of the invention. The description below is included to provide further information about the present patent application.

Figure 1B:
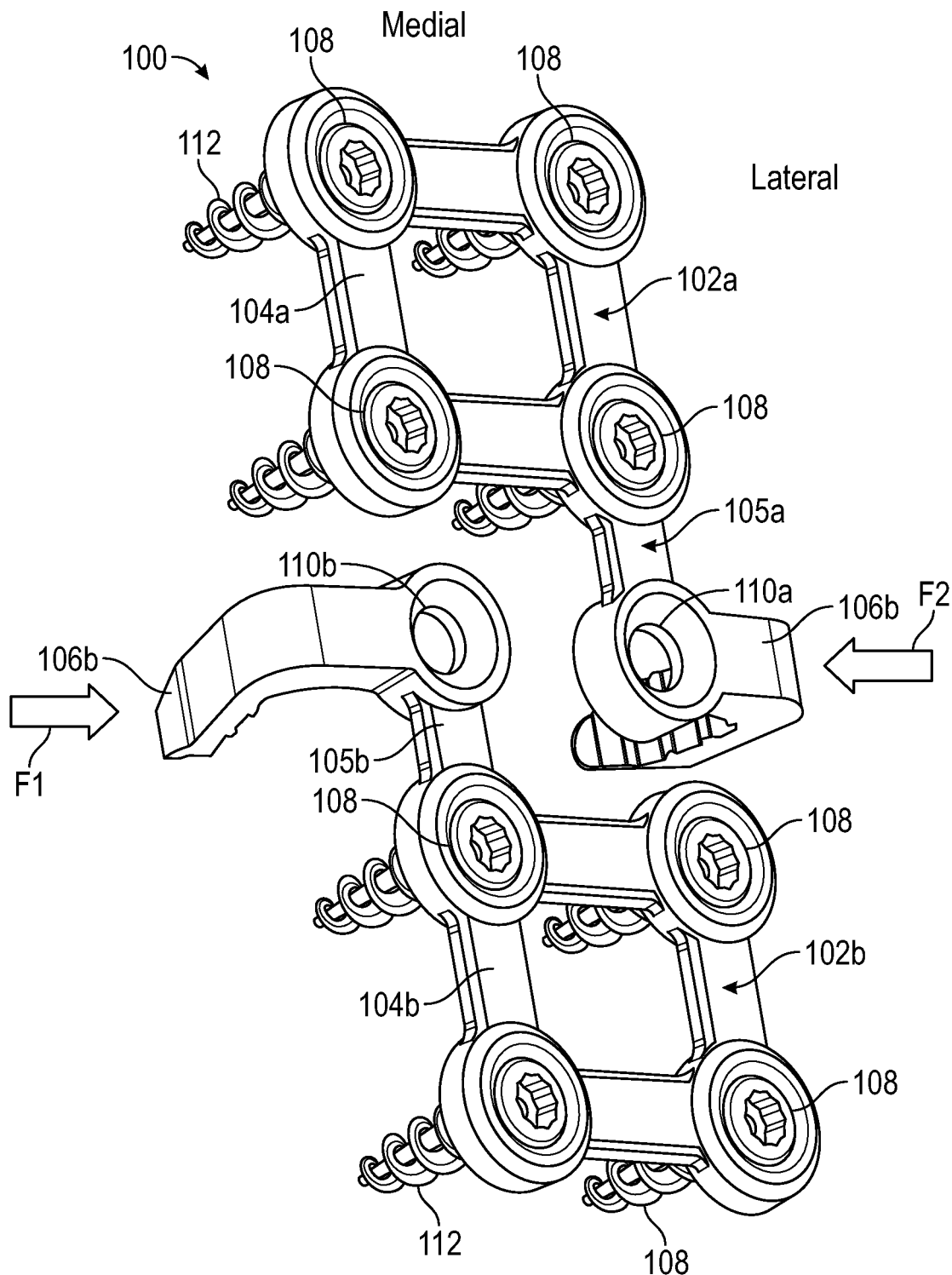
FIG. 1B illustrates an isometric view of a plating system.

FIG. 1A illustrates an isometric view of a sternum 50 and plate system 100. FIG. 1B illustrates an isometric view of the plate system 100. FIGS. 1A and 1B are discussed below concurrently. Also shown in FIGS. 1A and 1B are forces F1 and F2. Also shown in FIG. 1B are orientation indicators Medial and Lateral.

The sternum 50 can include sternal portions 52a and 52b, ribs 54a-54n, and ribs 56a-56n. The plate system 100 can be a paired plate system including opposing pairs of plates securable to the sternum 50. Optionally, each pair of plates can include two opposing plates 102, but the plate system can also include multiple pairs of plates. Each plate 102 can each include a body 104 (e.g., body 104a of the plate 102a and body 104b of the plate 102b), a hook 106, fastener bores 108, reduction bores 110, and fasteners 112. The plate system 100 can also include fasteners 112.

The body 104 can be a rigid or semi-rigid body. The body 104 can be made of materials such as metals, plastics, foams, elastomers, ceramics, composites, or combinations thereof. In some examples, the body 104 can be comprised of biocompatible materials such as such as one or more of stainless steels, cobalt-chromium, titanium variations, polyether ether ketone (PEEK), polyether ketone ketone (PEKK), or the like. In one example, the body 104 can be comprised of PEEK and can be coated with titanium and/or a hydroxyapatite coating.

The body 104 can be shaped such that the bores 108 form a rectangular or square pattern, either of which can be pre-contoured to match the anatomy of the sternum. Optionally, the plate can be elongate, such as a plate including two bores. The body 104 can be shaped such that the bores 108 form other shapes in other examples, such as an X pattern, JL pattern, hexagonal pattern, Y pattern, V pattern, or the like. An extension 105 can extend from the body, such as from one of the bores 108 and can be connected to the hook 106 and the reduction bore 110 such that the hook 106 and reduction bore 110 are extended from the body 104. The plates 102a and 102b can be the same shape such that when the plate 102b is rotated 180 degrees the hooks 106a and 106b can be positioned directly across from each other or can be in alignment or substantially in alignment. Substantially in alignment can be aligned in one or more planes or can mean in alignment on one plane and in alignment within 5, 10, 15, 20, or the like degrees.

The hook 106 can be formed of similar materials to the body 104 and can be optionally integrally formed with the body 104. The hook 106 can be located adjacent (or near or in alignment with) the reduction bore 110. The hook 106 can extend laterally outward from the body 104, distally away from the body 104, and then laterally back towards the body 104 such that the hook 106 can form a C-shape or a hook shape that is open towards the body 104. Optionally, the hook 106 can include barbs or serrations to help increase friction between the hook 106 and bone.

The fastener bores 108 can extend through portions of the body 104 and can be configured to receive a fastener (e.g., fastener 112) therethrough. Optionally, the fastener bores 108 can include threading for interfacing with threading of the fasteners 112. Optionally, the body 104 can be wider at the portions around the bores 108 and narrower at the portions connecting the bores 108, which can help reduce weight of the plate 102. As shown in FIG. 1B, the plate 102 can include four fastener bores. Optionally, the plate 102 can include 1, 2, 3, 4, 5, 6, 7, 8, 9, 10, or the like fastener bores. In an example where the plate 102 includes only 1 fastener bore, the reduction bore 110 can be used as a second fastener bore where the fastener bore is located on one side of a sternotomy and the reduction bore is located on the opposite side of the sternotomy.

The reduction bore 110 can be a bore located near the hook 106, as discussed above and as shown in FIG. 1B. The reduction bore 110 can be configured to receive a portion of a reduction tool to secure the reduction tool to the plate 102 and to be easily decoupled from the plate 102 after fixation. Optionally, the reduction bore 110 can be a threaded bore and can be configured to receive a fastener therethrough, such as following use of the reduction bore 110 for reduction of sternal halves.

During a sternotomy, a midline cut or resection 58 of the sternum 50 can be performed to separate the sternum 50 before a cardiac procedure is performed. In some examples, a cut guide can be used to create the midline cut 58 or create bone tunnels 60. Following the cardiac or other procedure, when the sternum 50 must be closed, the plates 102 can be attached to a reduction tool and the plates 102 can be positioned such that the bone hooks 106 are in alignment and are engaged with the sternal halves 52a and 52b.

More specifically, the bone hook 106a can engage a lateral portion of the sternal half 52a between ribs 54a and 54b (e.g., intercostally) and its opposing bone hook 106b can engage a lateral portion of the sternal half 52b between ribs 56a and 56b (e.g., intercostally). As discussed in further detail below, the plates 102a and 102b can be used together as a paired plate system where a reduction tool can be used to approximate and reduce the sternal halves 52a and 52b. Because the bone hooks 106 are substantially in alignment, engagement of the sternal half 52a by the bone hook 106a can be equal and opposite to engagement of the sternal half 52b by the bone hook 106b. That is, the forces F1 and F2 applied to the sternal halves 52a and 52b by the hooks 106a and 106b, respectively, can be equal (or substantially equal) in magnitude and opposite (or substantially opposite) in direction.

Once the sternal halves 52a and 52b are together and the opposing forces maintained firmly through the hooks 106 with the reduction tool (e.g., 200), the fasteners 112 can be secured to the sternal halves 52a and 52b through the bores 108 of both plates 102a and 102b and of the other plates, to secure the sternal halves 52a and 52b in medial-lateral directions, super-inferior directions, and anterior-posterior directions. This is achieved, in part, by securing of fasteners of each plate on both sides of the sternum 50. For example, fasteners 112 can be secured through two bores of the plate 102a to the sternal half 52a and through two adjacent bores of the plate 102a to the sternal half 52b, and likewise for its opposing plate 102b. Furthermore, each of the plates in this pair can have the additional stability and support provided by the opposing hooks 106. Such fixation can help to limit relative movement of the sternal halves 52a and 52b. Optionally, the reduction bores 110 can receive fasteners therethrough for additional fixation to the sternum 50.

The plates 102 can be shaped such for each plate, half of the bores 108 can be located on the sternal half 52a and the other half of the bores 108 can be located on the sternal half 52b while avoiding contact between plates and while allowing the reduction bores 110a and 110b to be aligned to align forces F1 and F2. This shape can allow for full reduction of the sternal halves 52 using the paired plates 102 by helping to avoid contact of the plates 102a and 102b with each other.

Though the plates 102 (or pairs of plates) are discussed above (and below) as being configured to secure to, approximate, and reduce a sternotomy, the plates 102 can be used to repair other bone fractures such as rib fractures, manubrium fractures, or other bone fractures. The plates, plate systems, and methods discussed below can also be used to repair various bone fractures in addition to sternum fractures.

Figure 2A:
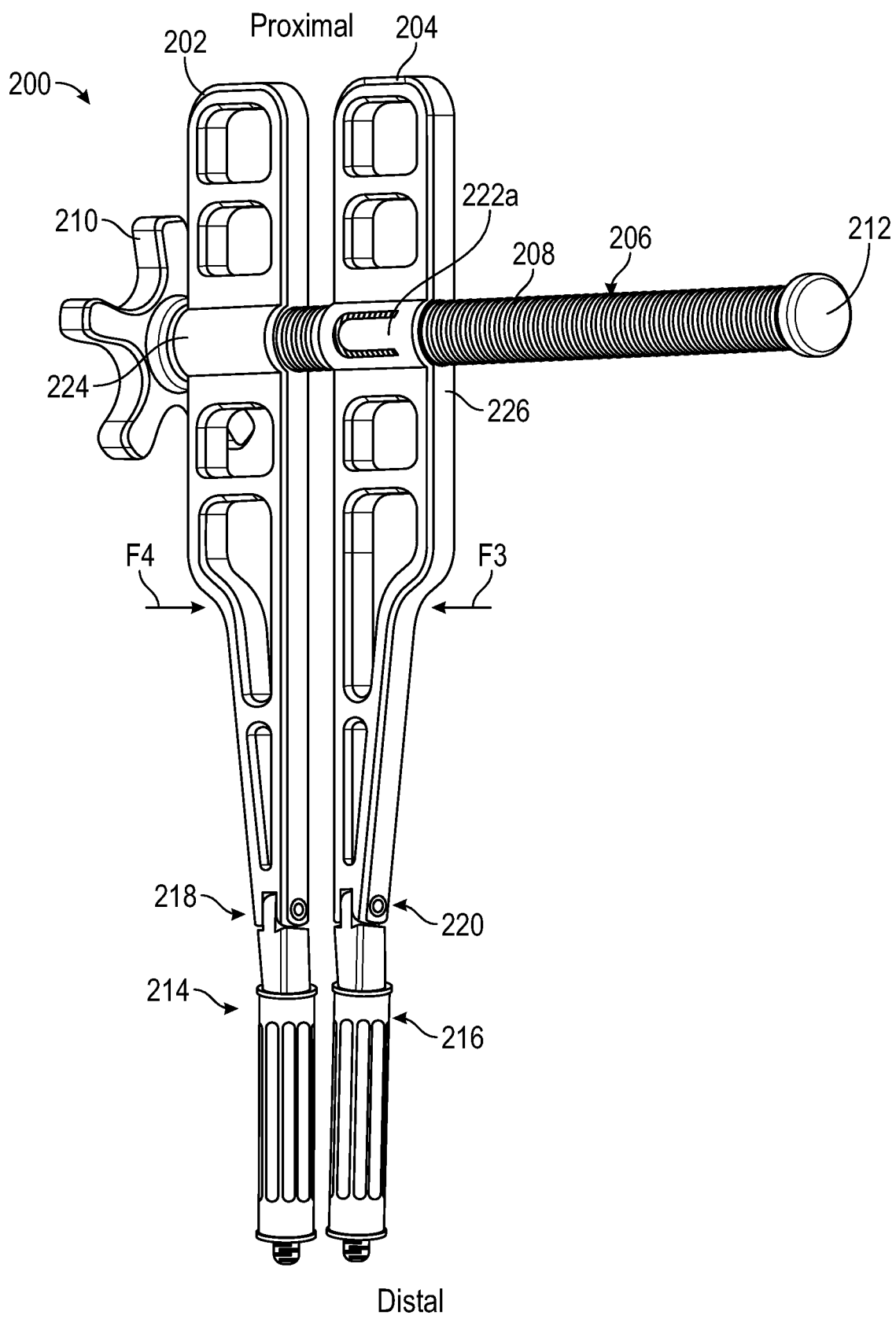
FIG. 2A illustrates an isometric view of a reduction tool.
Figure 2B:
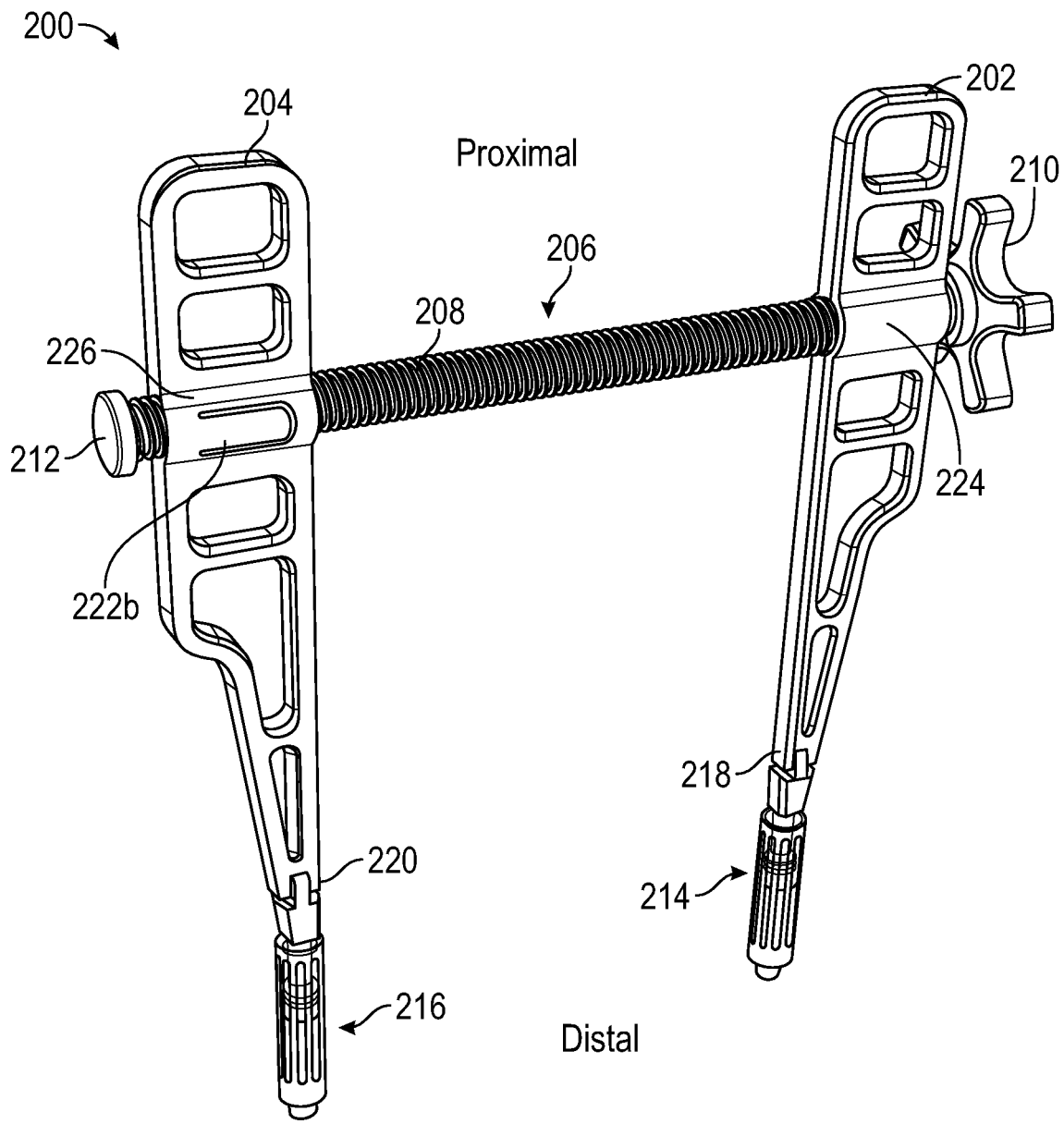
FIG. 2B illustrates an isometric view of a reduction tool.

FIG. 2A illustrates an isometric view of a reduction tool 200 in a closed position. FIG. 2B illustrates an isometric view of the reduction tool 200 in an open position. FIGS. 2A and 2B are discussed together below.

The reduction tool 200 can include handles 202 and 204 and an actuator 206. The actuator 206 can be a threaded rod assembly (for example) including a threaded rod 208, a knob 210, and a stop 212. The handle or arm 202 can include a reduction feature 214 and a hinge 218 and the arm 204 can include a reduction feature 216 and a hinge 220. The handle or arm 204 can include tabs 222a and 222b.

The components of the reduction tool 200 can be made of materials such as metals, plastics, foams, elastomers, ceramics, composites, or combinations thereof. In some examples, the body 104 can be comprised of biocompatible materials such as such as one or more of stainless steels, cobalt-chromium, titanium variations, polyether ether ketone (PEEK), polyether ketone ketone (PEKK), or the like.

The handles 202 and 204 can be shaped to be grasped by hands and can optionally be tapered as the handles 202 and 204 extend distally. Optionally, the handles 202 and 204 can be skeletonized to help reduce a weight or mass of the handles 202 and 204. The handles 202 and 204 can also include sleeves 224 and 226, respectively, which can define bores extending therethrough. The sleeves 224 and 226 can be sized and shaped to receive the threaded rod 208 of the actuator 206 therethrough. The sleeve 224 can be internally threaded to form a threaded interface with the threaded rod 208. Optionally, the sleeve 224 can be free of threads such that the rod 208 can freely spin in the sleeve 224 but the sleeve 224 can be axially fixed on the rod 208 such that the rod 208 is captured or captivated by the sleeve 224 but free to rotate therein.

Figure 2C:
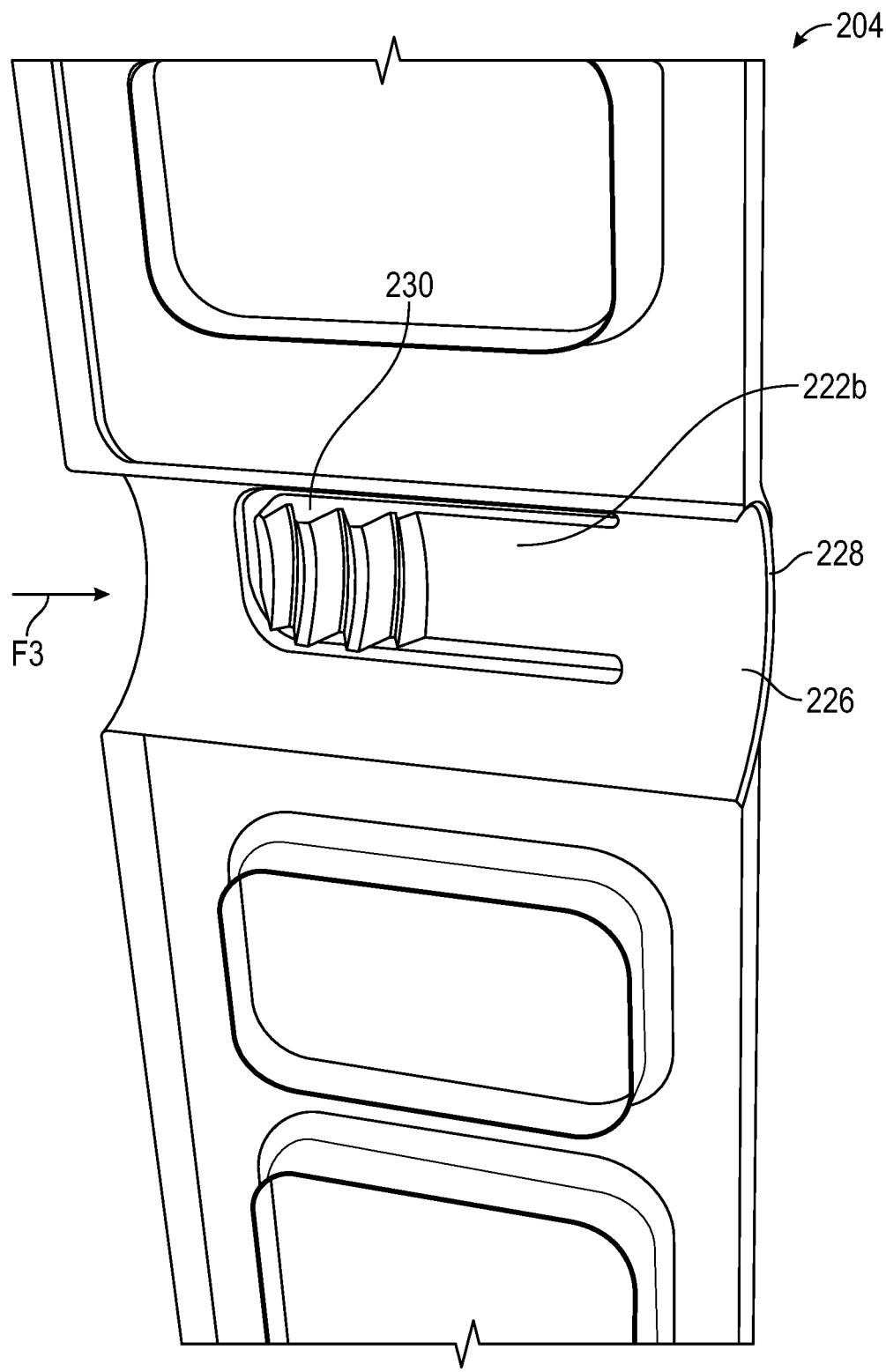
FIG. 2C illustrates an enlarged cross-sectional view of a reduction tool.

As shown in FIG. 2C, the sleeve 226 can define the bore 228 extending therethrough. An internal portion of the sleeve 226 can be smooth and an inner portion of the tabs 222 can be threaded such that threading 230 can form a threaded engagement between the tabs 222 and the threaded rod 208. Threading 230 can be relatively flat on one face and can be ramped on an opposite face such that an axial force F3 can allow the threading 230 to pass over threading of the threaded rod 208. During this process, the tab (e.g., tab 222b) can deflect outward from the sleeve 226 to allow the threads 230 to move outward to allow the rod 208 to translate through the bore 228 without threading. This deflection of the tabs 222 can create a ratcheting interface with the threaded rod 208. Forces in directions opposite to the forces F3 and F4 will be prevented or limited from ratcheting by engagement between the threaded rod 208 and flat surfaces of the threading 230 of the tabs 222.

Optionally, the tabs 222 can include levers or other features that allow a user to move the tabs 222 to disengage the tabs 222 from the rod 208. Such disengagement of the tabs 222 from the rod 208 can allow the handle 204 to move freely toward or away from the handle 202 along the rod 208. The lever or other feature can be releasable to allow the tabs 222 to return to a position where the tabs are engaged with the threaded rod 208. Optionally, the tabs 222 can be biased to a position where the tabs 222 are engaged with the threaded rod 208. Such a release feature can allow for the handles 202 and 204 to be quickly adjusted with respect to each other, such as to quickly open or separate the handles 202 and 204 prior to beginning approximation of the sternal halves 52.

Referring back to FIG. 2A, when the force F3 is applied to the handle 202 and a force F4 is applied to the handle 204, the handles 202 and 204 can be quickly moved towards each other as the threaded rod 208 passes over the tabs 222 in a ratcheting manner. This function can be used when approximating the sternal halves.

More specifically, the handles 202 and 204 can be in a separated configuration or position, such as where the handle 202 engages the knob 210 and the handle 204 engages the stop 212 for reaching maximum aperture to accommodate largely separated sternal halves, as shown in FIG. 2B. When the handles 202 and 204 are in the separated configuration, as shown in FIG. 2B, the forces F3 and F4 can be applied to the handles 202 and 204 to cause the ratcheting mechanism formed by the threaded rod 208 passing over the tabs 222 allowing for relatively quick movement of the handles 202 towards each other and therefore relatively quick movement of the sternal halves 52 towards each other for relatively quick approximation of the sternal halves. Once the halves 52 are approximated using the ratcheting function or features, the knob 210 or handle 210 can be operated to rotate the rod 208 to threadably engage the threading 230 of the tabs 222 to draw the handle 204 toward the handle 202 until the sternal halves 52 are in a desired (e.g., contacting) position, helping to achieve full approximation of the sternal halves.

Because the actuator 206 can use a threaded rod 208 for reduction of the handles 202 and 204 (and therefore of sternal halves 52), the actuator 206 can provide fine resolution (e.g., infinite control) for applying compressive forces applied by to the plates 102 and therefore to the sternal halves 52, allowing a physician or surgeon to select or achieve desired reduction forces before securing the plates 102 to the sternal halves using fasteners.

Figure 2D:
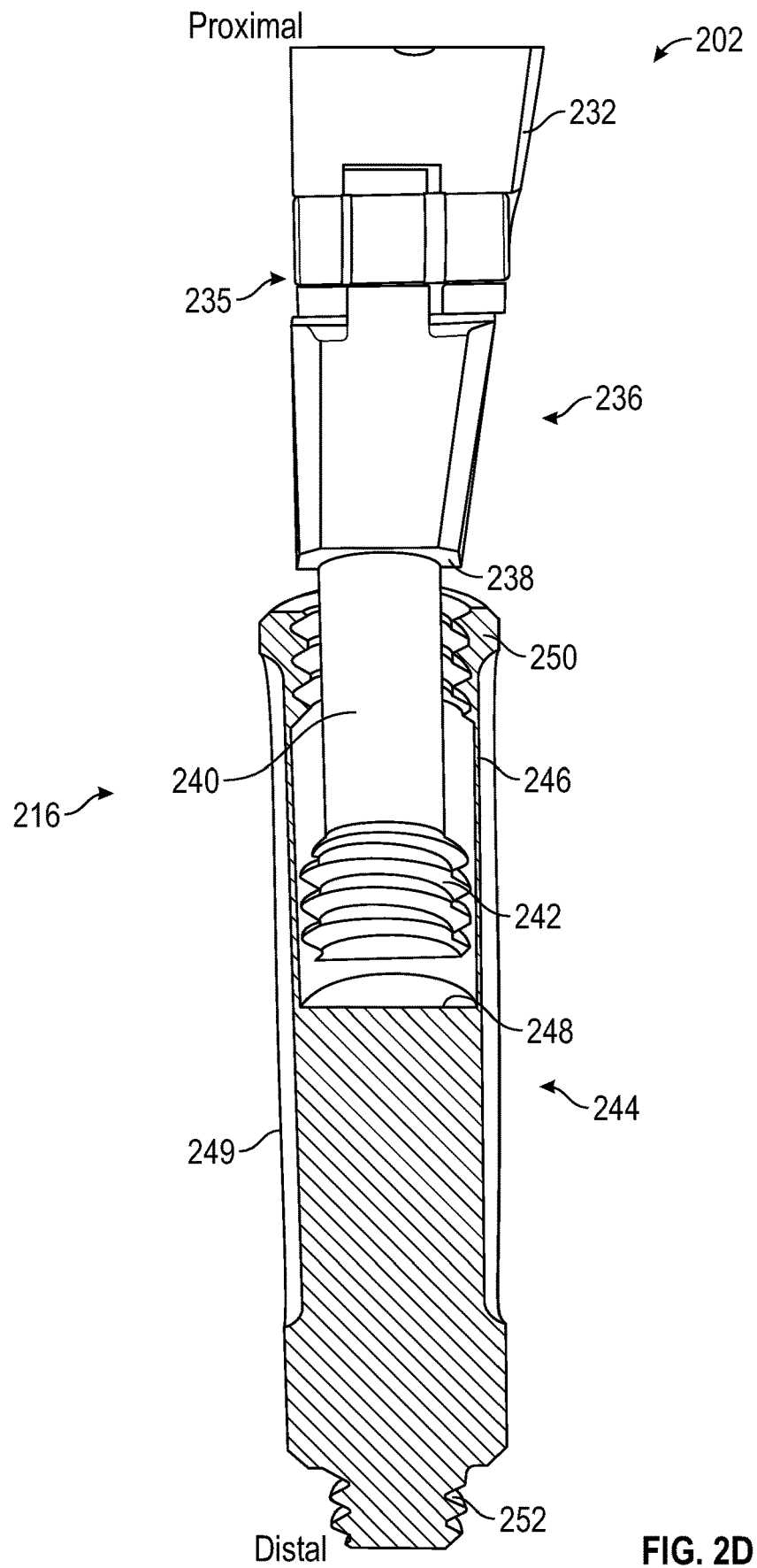
FIG. 2D illustrates a cross-sectional view of a reduction tool.

FIG. 2D shows the reduction feature 216. A distal portion 232 of the handle 202 can be connected to the reduction feature 216 by connecting to a leg 236 by a hinge 235. The hinge 235 can be formed by a pin and knuckles, but can be other types of hinges in other examples. The leg 236 can include a shoulder portion 238, a shaft 240, and a distal threaded portion 242. FIG. 2D also shows an actuator 244 that can include a bore 246 extending into a body 249 of the actuator 244. The bore 246 can include a threaded portion 250 at a proximal portion of the bore 246. The bore 246 can include a distal termination 248. The actuator 244 can also include a projection 252, which can optionally be a threaded projection configured to threadably engage the reduction bores 110 of the plates 102.

The threaded portion 250 of the bore 246 can be threaded on to the threaded portion 242 of the leg 236 until the threaded portions 242 extends into the bore 246 beyond the threaded portion 250 at which point the leg 236 can be free to translate with respect to the actuator 244. Translation of the actuator 244 with respect to the leg 236 can be limited in a distal direction by contact between the threaded portion 242 of the leg 236 and the threaded portion 250 of the bore 246. Proximal translation of the actuator 244 with respect to the leg 236 can be limited by contact between a proximal portion of the actuator 244 and the shoulder 238 or by the distal portion 248 of the bore and the threaded portion 242. This translation can allow leeway for disengaging/decoupling/unthreading the threads 252 from the reduction bores 110 of the plates 102.

Figure 3A:
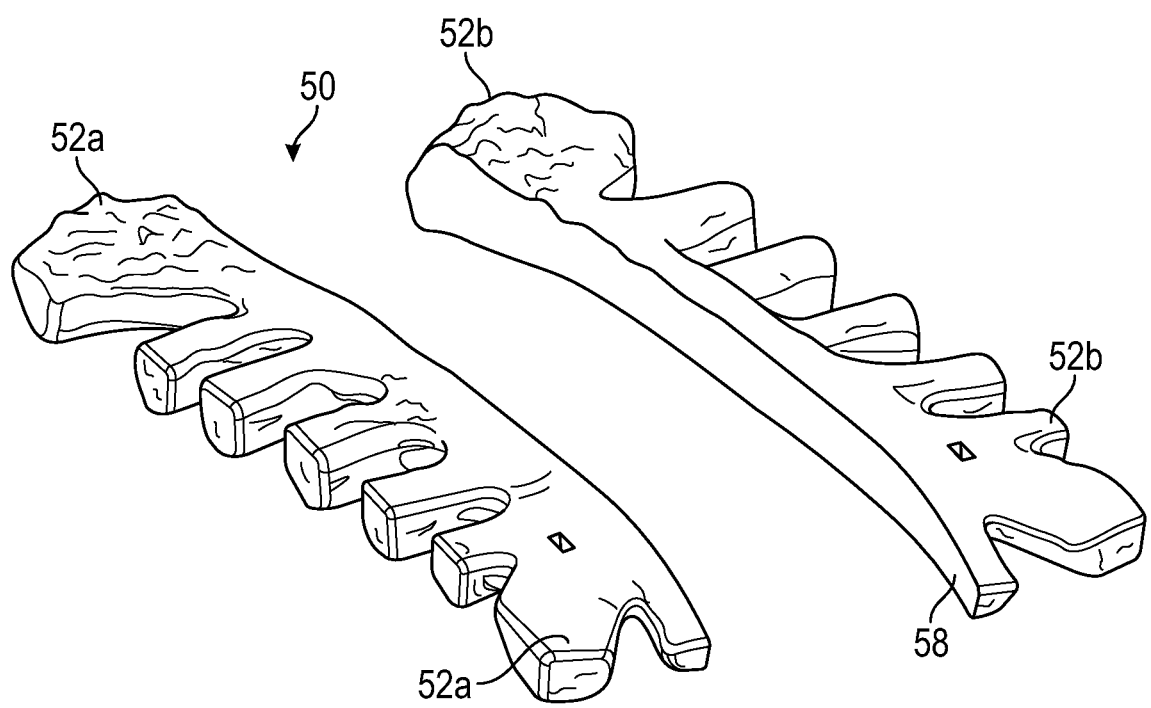
FIG. 3A illustrates an isometric view of a sternum.
Figure 3B:
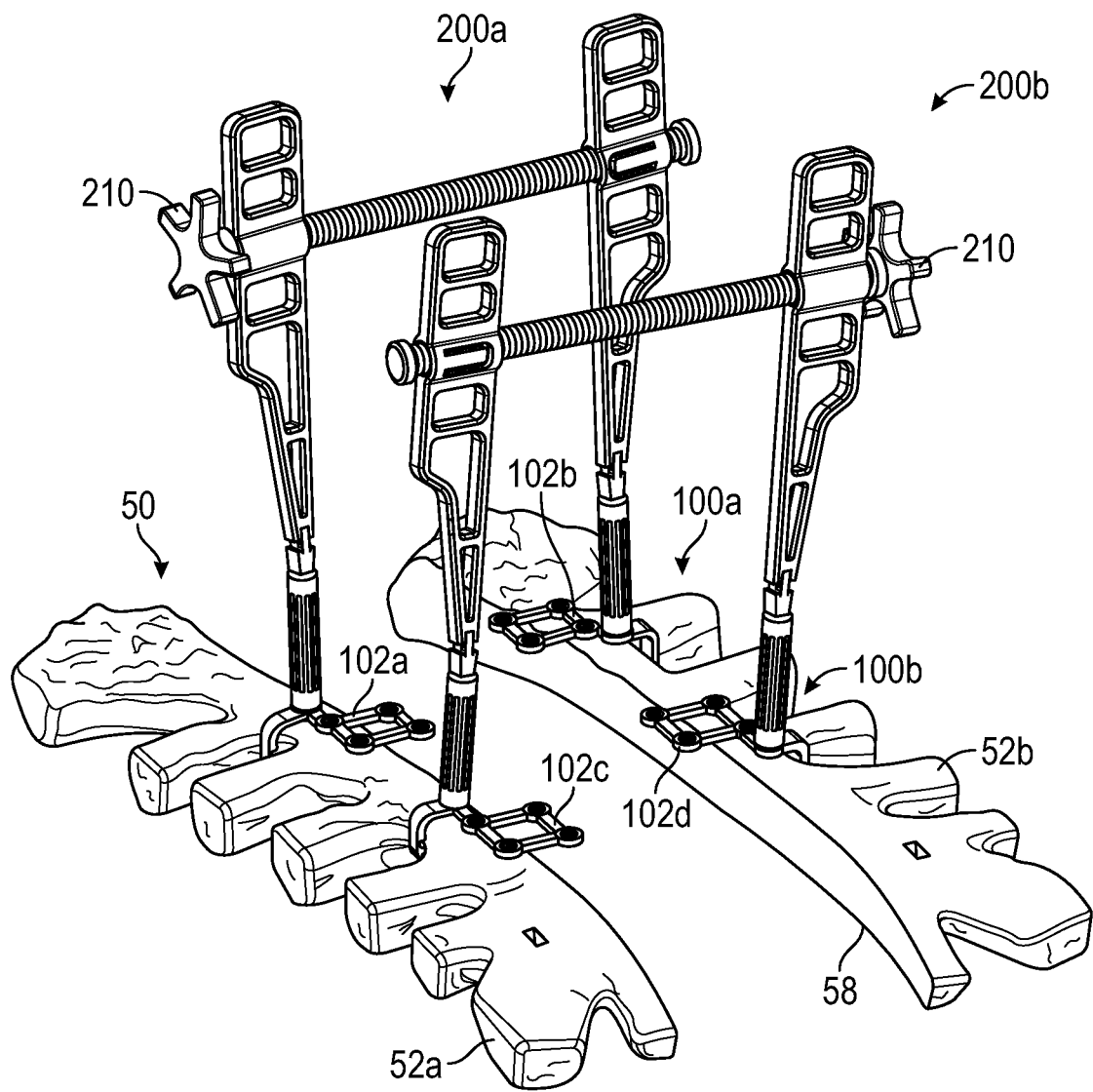
FIG. 3B illustrates an isometric view of a sternum and plating system.
Figure 3C:
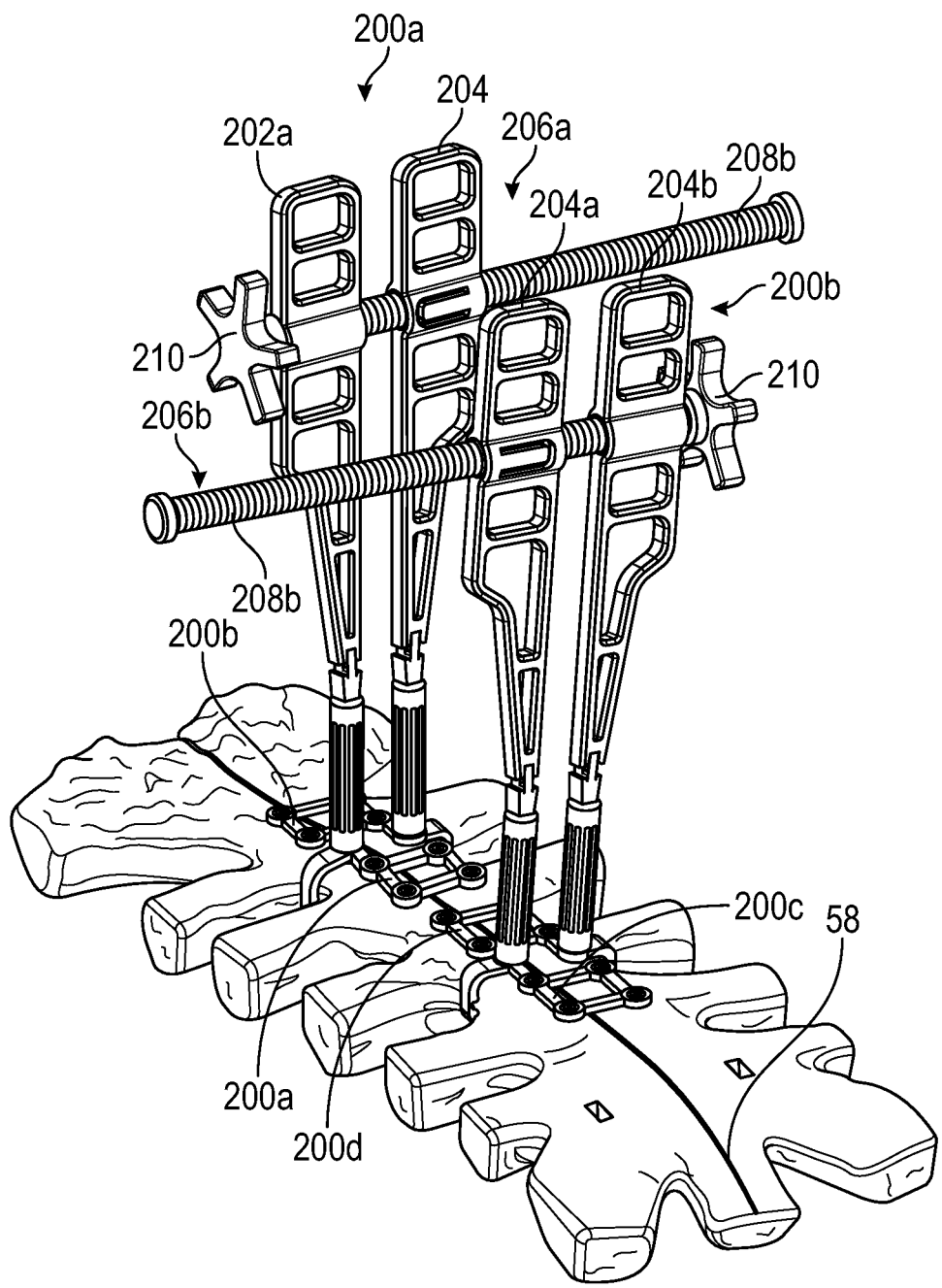
FIG. 3C illustrates an isometric view of a sternum and plating system.
Figure 3D:
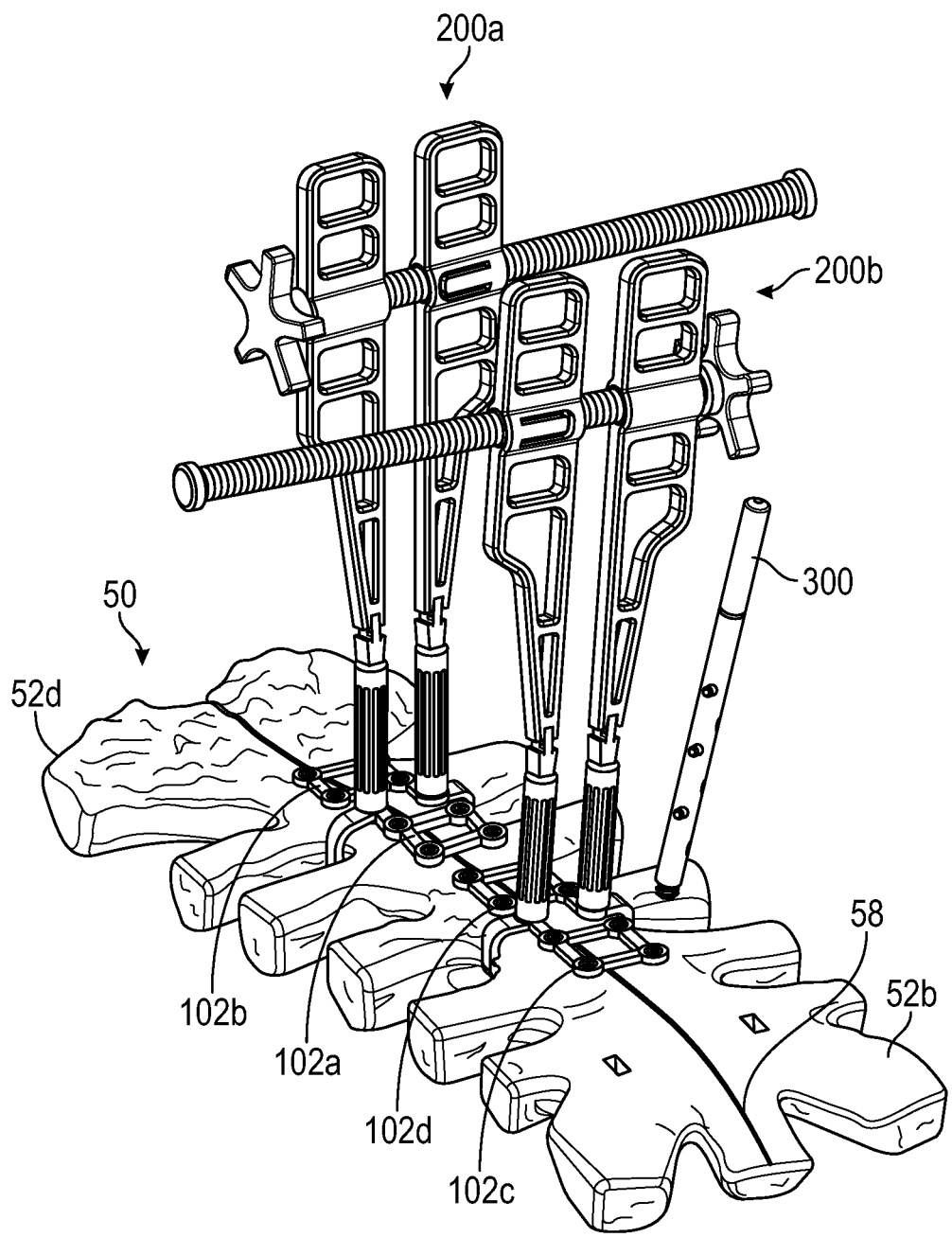
FIG. 3D illustrates an isometric view of a sternum and plating system.
Figure 3E:
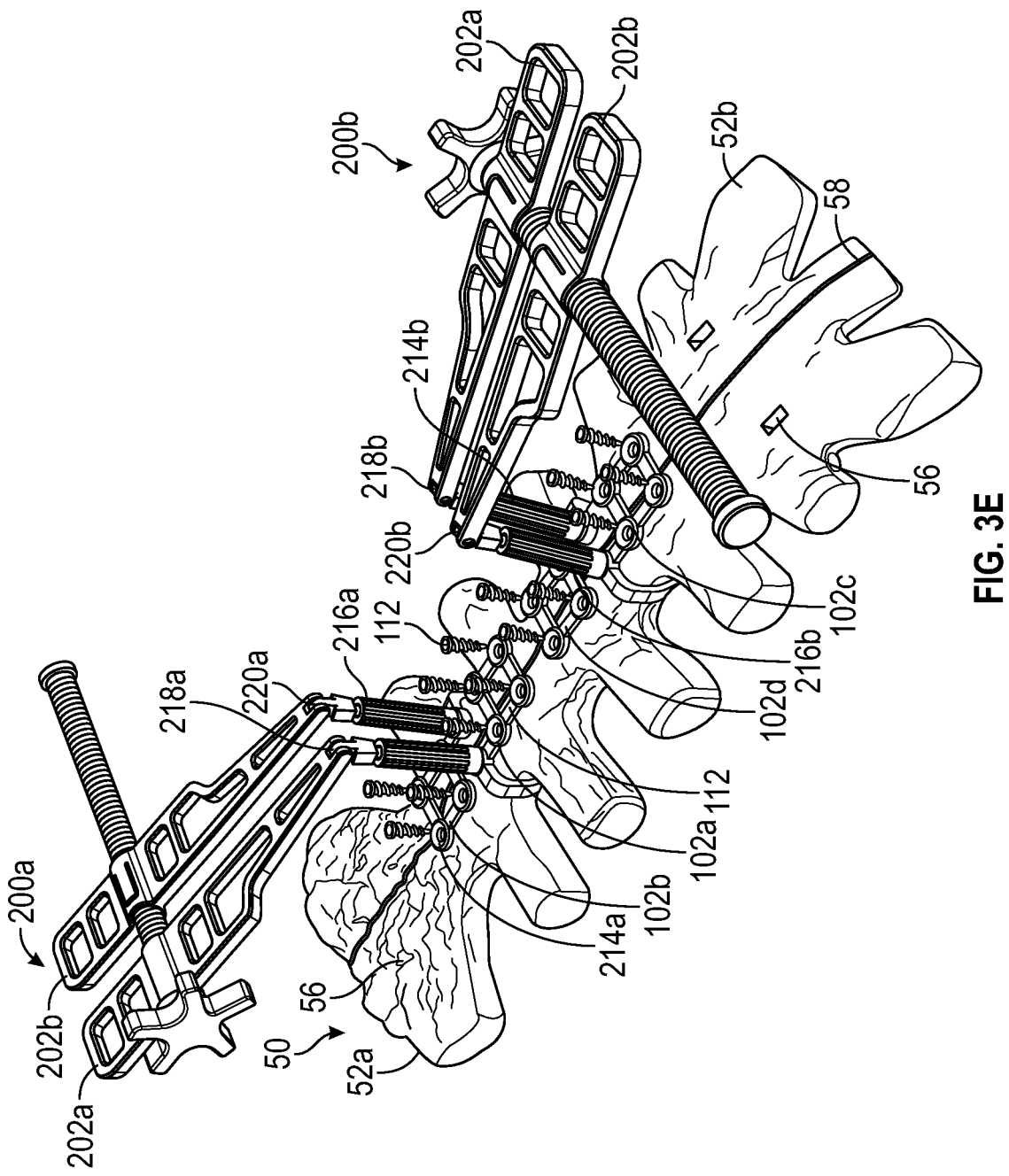
FIG. 3E illustrates an isometric view of a sternum and plating system.
Figure 3F:
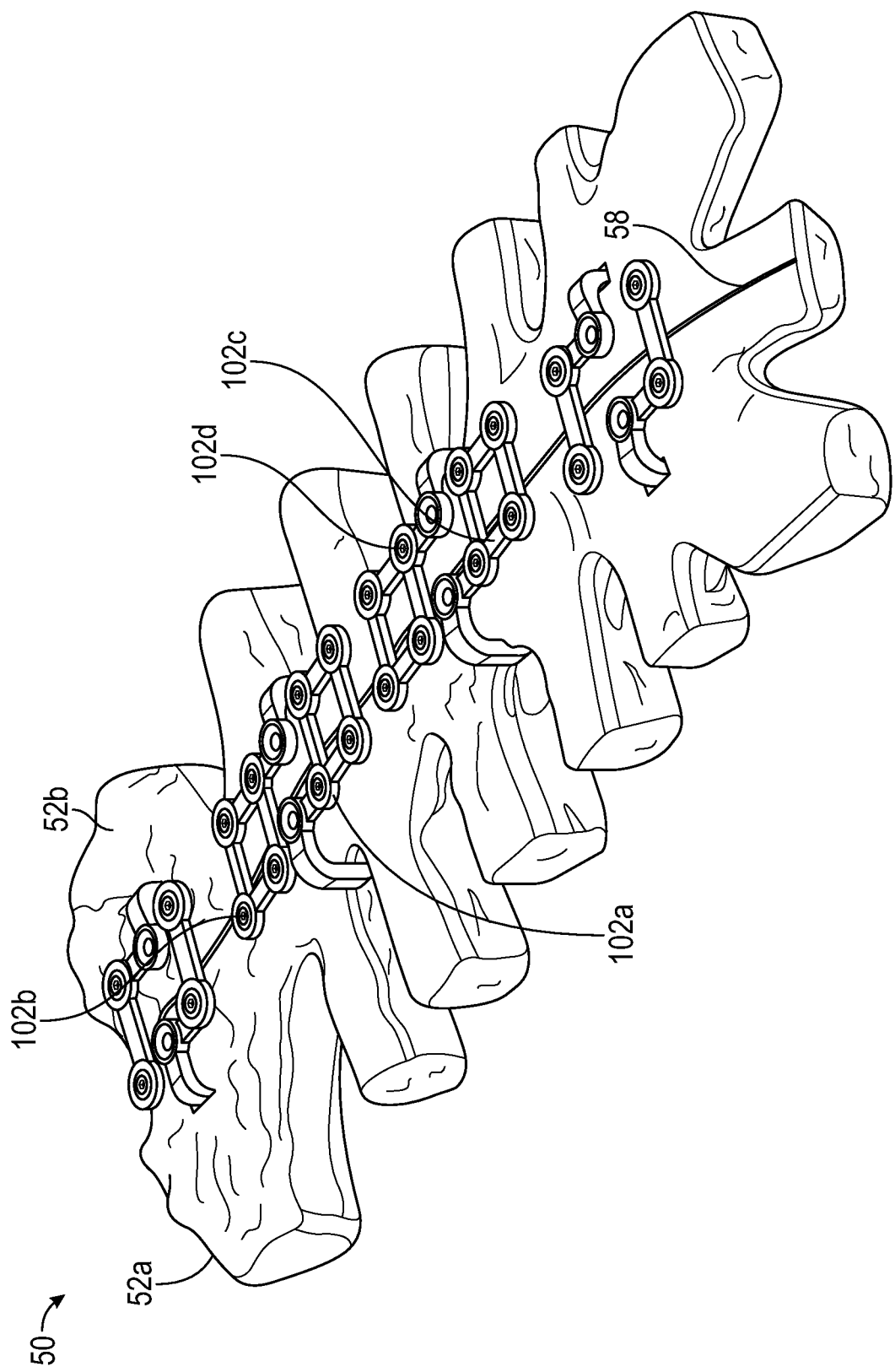
FIG. 3F illustrates an isometric view of a sternum and plating system.

FIG. 3A illustrates an isometric view of the sternum 50. FIG. 3B illustrates an isometric view of the sternum and the plating system 100 and the reduction tool 200. FIG. 3C illustrates an isometric view of the sternum 50, the plating system 100, and the reduction tool 200. FIG. 3D illustrates an isometric view of the sternum 50, the plating system 100. FIG. 3E illustrates an isometric view of the sternum 50, plating system 100, and reduction tool 200. FIG. 3F illustrates an isometric view of the sternum 50, plating system 100, and reduction tool 200. FIGS. 3A-3F are discussed together below.

As shown in FIG. 3A, the sternum 50 can be cut along the cutline 58 to create the sternal halves 52*a* and 52*b*, such as prior to a cardiac procedure. Following the cardiac procedure (or other procedure, or when it is otherwise desired to close the sternum 50), the plates 102 can be secured to the reduction tools 200, such as in pairs. For example, the projection 252 (shown in FIG. 2D) can be positioned in one of the reduction bores 110, such as the reduction bore 110*a* of the plate 102*a* (shown in FIG. 2B). The actuator 244 can then be rotated with respect to the leg 236, and therefore the handle 202, to cause rotation of the projection 252, allowing the projection 252 to thread into the reduction bore 110*a*. This process can be repeated for each plate. For example, the reduction tool 200*a* can be secured to the plates 102*a* and 102*b* and the reduction tool 200*b* can be secured to the plates 102*c* and 102*d*, as shown in FIG. 3B. Optionally, the reduction tools 200*a* and 200*b* can be arranged in opposing directions to help balance forces applied to the plates 102 (and the sternal halves 52) by the reduction tools 200 during approximation and reduction of the sternal halves 52.

Once the plates 102 are secured to the reduction tools 200, the plates 102 can be positioned to engage the sternal halves such that the hooks 106 engage lateral portions of the sternal halves, as shown more clearly in FIG. 1A. In this configuration, each pair of plates (e.g., plates 102*a* and 102*b*) can have hooks that are arranged in substantially opposing directions and configurations to allow opposing forces to be applied to the sternal halves 52*a* and 52*b* by the hooks 106*a* and 106*b*, as shown in FIGS. 1A and 1B.

The knobs 210*a* and 210*b* can be rotated to drive the threaded rods 208*a* and 208*b* of the actuators 206*a* and 206*b* of the reduction tools 200*a* and 200*b*, respectively. Rotation of the knob 210*a* can create linear movement of the handles 202*a* and 204*a* towards each other, as described above. The knobs 210*a* and 210*b* can be rotated until the sternal halves 52*a* and 52*b* contact each other or until the surgeons or the physicians choose. Such positioning can cause the plates 102 to be positioned such that two bores 108 of each plate are on each sternal half 52*a* and 52*b*, as shown more clearly in FIG. 1A. Optionally, the knobs 210*a* and 210*b* can be rotated in the opposite direction to move the sternal halves 52*a* and 52*b* away from each other, such as to make an alignment adjustment of the sternal halves 52*a* and 52*b*. Such actions can be repeated, as required or desired.

Once the plates 102 are positioned as desired, the plates 102*a*-102*d* can be bent, such as by using an instrument 300, as shown in FIG. 3D, to help match the plates 102*a*-102*d* to a shape of the sternum 50 of the patient. When the plates 102 are located and positioned with respect to the sternum 50, the plates 102 can be secured to the sternal halves 52 using fasteners 112. To help provide access to the plates 102 to secure the fasteners 112 through the bores 108 and into the sternal halves, the handles 202 and 204 can rotate about the hinges 218 and 220 (e.g., 235) while the reduction features 214 and 216 remain connected to the reduction bores 210.

Optionally, bone tunnels 56 can be created in superior and inferior portions of the sternum 50. The bone tunnels 56 can be shaped and sized to receive bone hooks of plates for additional securing of the sternal halves 52*a* and 52*b*. Once the fasteners 112 are secured through the plates 102, the reduction tools 200 can be disconnected from the plates 102 by operating the actuator 244 (shown in FIG. 2D) to unthread the projections 252 from the reduction bores 110, leaving the plates 102 secured to the sternal halves (as shown in FIG. 3F). Optionally, once the reduction tools 200 are removed from the plates 102, the reduction bores 110 can receive fasteners 112 therethrough to further secure the plates 102 to the sternum 50.

Figure 4:
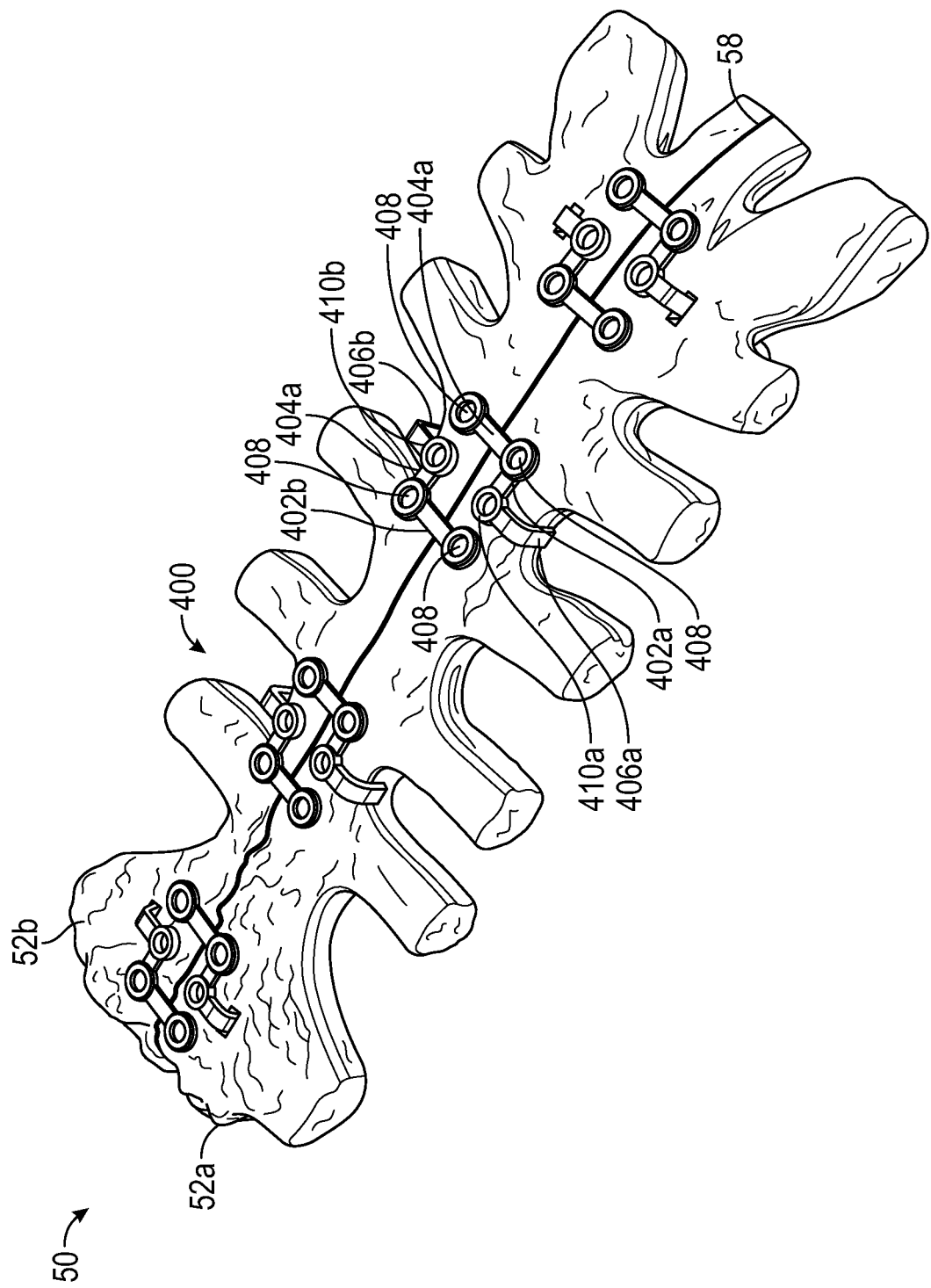
FIG. 4 illustrates an isometric view of a plating system.

FIG. 4 illustrates an isometric view of a plating system 400. The plating system 400 can be similar to the plating system 400 of FIGS. 1A-3F; the plating system 400 can differ in that plates 402*a* and 402*b* can include fewer fastener bores.

That is, for example, the plate 402*a* can include a body 404*a* that defines two fastener bores 408 and a reduction bore 410*a*. The fastener bores 408 can be configured to be positioned on opposite sides of the sternotomy 58 for securing the plate 402*a* to each of the sternal halves 52*a* and 52*b*. The plates 402 can be used similarly to the plates 102 described above, but the plates 402 can receive fewer fasteners, which can help to reduce an amount of time required to secure the plates 402 to the sternum 50, and can help to reduce the number of components secured to the sternum 50 of the patient, which can help to improve healing and patient comfort.

Figure 5:
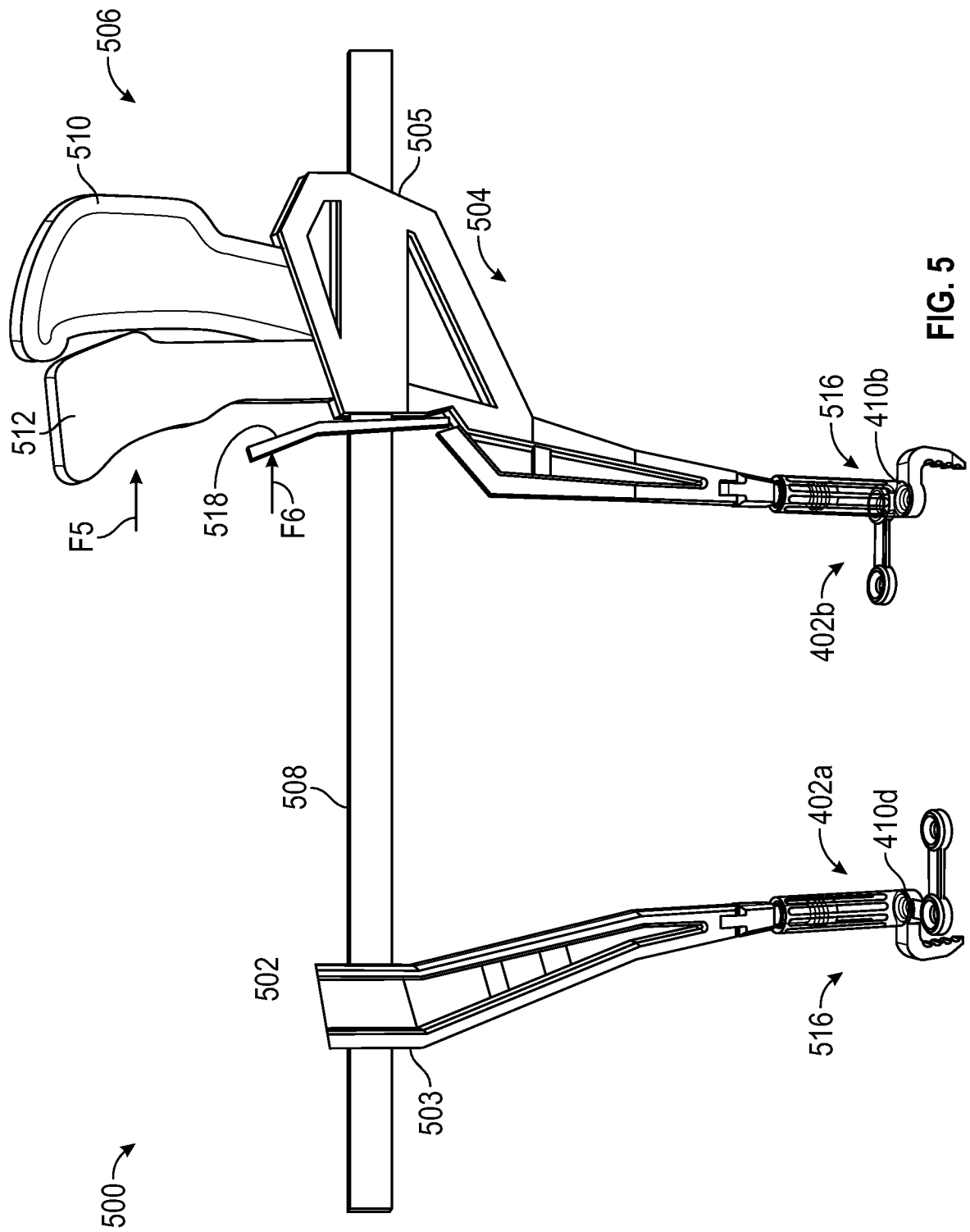
FIG. 5 illustrates an isometric view of a reduction tool.

FIG. 5 illustrates an isometric view of a reduction tool 500. The reduction tool 500 can be similar to the reduction tool 200 described above; the reduction tool 500 can differ in that the tool can include a bar and friction plate mechanism.

More specifically, the reduction tool 500 can include handles 502 and 504. The handle 502 can include a bore 503 extending therethrough and the handle 504 can include a bore 505 extending therethrough. An actuator 506 can be connected to the handle 504. The actuator 506 can include a bar 508 extending through the bores 503 and 505 of the handles 502 and 504, respectively. The actuator 506 can also include a handle 510 and a lever or trigger 512. The lever 512 can be movable into the handle 510 or with respect to the handle 510. The lever can be biased to the extended position shown in FIG. 5. Similarly, a plate 518 can be operated to unlock the actuator 506 but can be biased to a locked position, as shown in FIG. 5.

In operation, when it is desired to use the reduction tool 500 to move the plates 402*a* and 402*b* towards each other, the lever 512 can be moved in the direction of a force F5 into the handle 510 to move the handle 504 towards the handle 502. Such movement can cause the bar 508 to be pulled through the handle 504 (such as using an internal friction plate and spring mechanism). The bar 508 can be secured to the handle 502 such that movement of the bar 508 through the handle 504 can cause the handles 504 and 502 to move towards each other. The lever 512 can be released and can return to the outward position of FIG. 5 where the lever 512 can be actuated again to move the handles 502 and 504 towards each other again. This process can be repeated until sternal halves (e.g., 52*a* and 52*b* contact each other) or until a physician otherwise decides to stop. When it is desired to move the handles 504 and 502 away from each other, the plate 518 can be moved using a force F6 to unlock the bar and allow the handles 504 and 502 to freely or easily translate away from each other, as guided by the bar 508. In this way, a physician or surgeon can quickly and easily reduce the plates 402 to help quickly and easily approximate and reduce sternal halves during a sternotomy repair.

Figure 6:
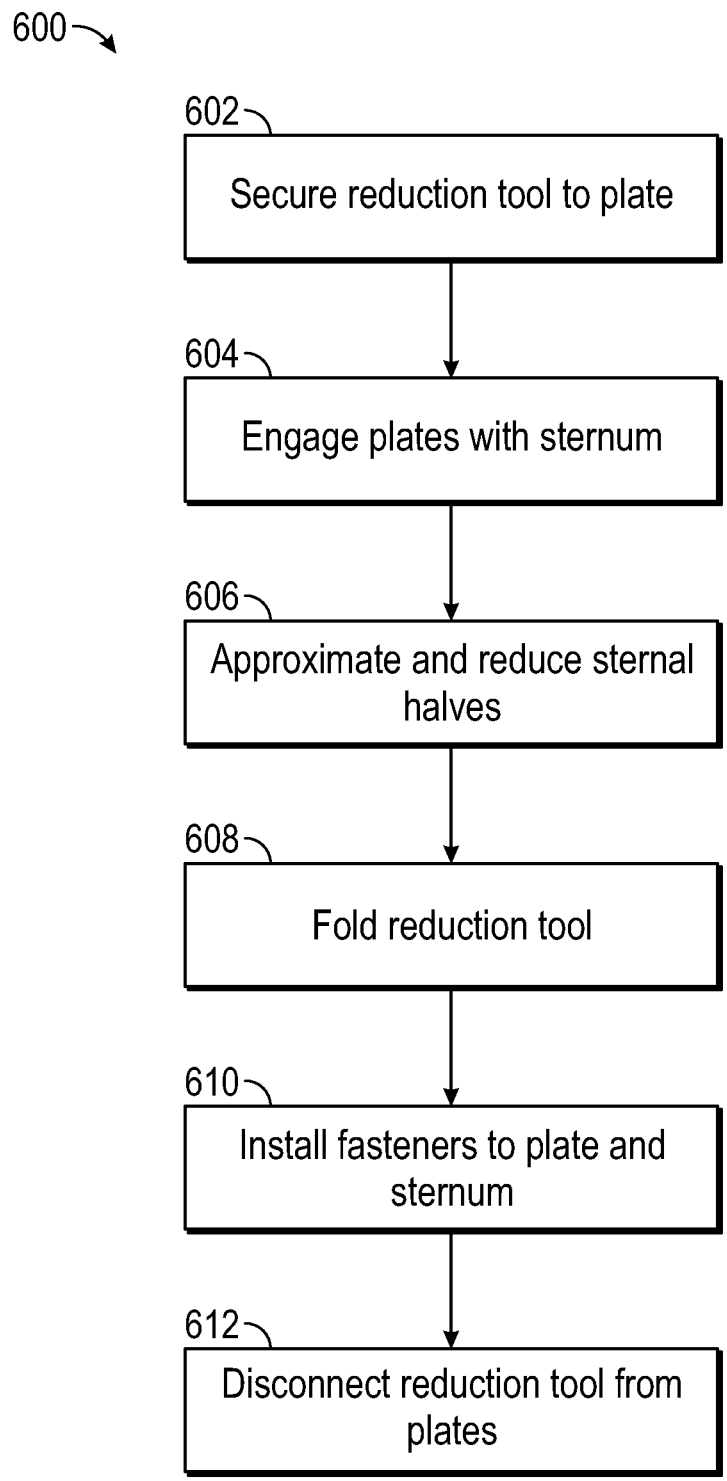
FIG. 6 illustrates a schematic view of a method.

FIG. 6 illustrates a schematic view of a method 600, in accordance with at least one example of this disclosure. The method 600 can be a method of repairing a sternotomy using a plating system and reduction tool. More specific examples of the method 600 are discussed above and below. The steps or operations of the method 600 are illustrated in a particular order for convenience and clarity; many of the discussed operations can be performed in a different sequence or in parallel without materially impacting other operations. The method 600 as discussed includes operations performed by multiple different actors, devices, and/or systems. It is understood that subsets of the operations discussed in the method 600 can be attributable to a single actor, device, or system could be considered a separate standalone process or method.

Prior to the steps of the method 600 being performed, a sternotomy or midline resection can be created in a sternum, such as the sternotomy 58 of the sternum 50. When it is desired to closer the sternum, step 602 can be performed where the a first feature of a first handle of a reduction tool can be secured to a first reduction bore of a first plate and a second feature of a second handle of the reduction tool can be secured to a second reduction bore of a second plate. For example, the reduction features 214 and 216 (e.g., projections 252) can be secured to reduction bores 110a and 110b of plates 102a and 102b.

At step 604, a first lateral portion of the first sternal portion can be engaged with a first bone hook of the first plate and a second lateral portion of the second sternal portion can be engaged with a second bone hook of the second plate. For example, the bone hooks 106a and 106b can engage lateral portions of the sternum 50.

At step 606, the first sternal portion and the second sternal portion can be reduced by operating the reduction tool to cause the first bone hook and the second bone hook to move the first sternal portion and the second sternal portion towards each other. For example, the sternal portions 52a and 52b can be reduced by operating the reduction tool 200 to cause the bone hooks 106a and 106b of the plates 102a and 102b, respectively, to apply medially directed forces to move the sternal halves 52a and 52b towards each other.

At step 608, the reduction tool can be folded at a hinge of the reduction tool while the reduction tool is attached to the first plate and the second plate. For example, the handles 202 and 204 of the reduction tool 200 can be folded at the hinges 218 and 220 while the reduction features 214 and 216 remain attached to the plates 102a and 102b. At step 610, a first fastener can be driven through a first bore of the first plate into the first sternal portion. For example, the fasteners 112 can be driven through bores 108 of the plates 102 to secure the plates 102 to the sternal halves 52. Optionally, bone punches can be used to create bone tunnels or bores in the manubrium or portion of the sternum and plates can be secured to the sternal halves with hooks of the plates located at least partially in the bone tunnels. At step 612 the reduction tool can be disconnected from the first plate and the second plate. For example, the reduction tool 200 can be disconnected from the plates 102a and 102b.

NOTES AND EXAMPLES

The following, non-limiting examples, detail certain aspects of the present subject matter to solve the challenges and provide the benefits discussed herein, among others.

Example 1 is a plate system for securing a first bone portion and a second bone portion of a separated bone structure, the plate system comprising: a first plate comprising: a first body defining: a first fastener bore configured to receive a first fastener for securing to the first bone portion; a second fastener bore configured to receive a second fastener for securing to the second bone portion; and a first reduction bore; and a first hook extending from the first body, the first hook engageable with a lateral portion of the first bone portion; and a second plate comprising: a second body defining: a third fastener bore configured to receive a third fastener for securing to the first bone portion; a fourth fastener bore configured to receive a fourth fastener for securing to the second bone portion; and a second reduction bore; and a second hook extending outward, or downward, or both, from the second body and extending distally from the second body, the second hook engageable with a lateral portion of the second bone portion opposite the first hook.

In Example 2, the subject matter of Example 1 optionally includes wherein the first hook extends outward from the first body adjacent the first reduction bore and wherein the second hook extends outward from the second body adjacent the second reduction bore.

In Example 3, the subject matter of any one or more of Examples 1-2 optionally include wherein the first plate includes a fifth fastener bore and a sixth fastener bore, the first fastener bore, the second fastener bore, the fifth fastener bore, and the sixth fastener bore arranged in a substantially rectangular configuration.

In Example 4, the subject matter of Example 3 optionally includes wherein the first reduction bore is aligned with the first fastener bore, the first reduction bore configured to be positioned on a same side of a midline resection as the first fastener bore and configured to be positioned on an opposite side of the midline resection from the second fastener bore.

In Example 5, the subject matter of Example 4 optionally includes wherein the first reduction bore is configured to be positioned on the opposite side of the midline resection from the second reduction bore.

In Example 6, the subject matter of any one or more of Examples 1-5 optionally include a reduction tool including: a first handle including a first feature that is insertable into the first reduction bore; and a second handle including a second feature that is insertable into the second reduction bore, the reduction tool operable to bring the first feature and the second feature together to cause the first hook and the second hook to engage the lateral portion of the first bone portion and the lateral portion of the second bone portion, respectively, to reduce the first bone portion and the second bone portion.

In Example 7, the subject matter of Example 6 optionally includes wherein the first handle includes a first hinge and the second handle includes a second hinge, the handles foldable at the first hinge and the second hinge while the first feature is connected to the first reduction bore and the second feature is connected to the second reduction bore.

In Example 8, the subject matter of any one or more of Examples 6-7 optionally include wherein the reduction tool includes an actuator operable to cause the first handle to move towards the second handle.

In Example 9, the subject matter of Example 8 optionally includes wherein the actuator is a threaded rod rotatable within the first handle and threadably engaged with the second handle such that rotation of the threaded rod causes the second handle to move towards the first handle.

In Example 10, the subject matter of Example 9 optionally includes wherein the first handle includes a tab including threading engageable with the threaded rod such that rotation of the threaded rod causes the first handle to move with respect to the second handle, the tab deflectable outward from the first handle to allow the first handle to be moved toward the second handle without rotation of the threaded rod, the tab configured to resist movement of the first handle away from the second handle without rotation of the threaded rod.

In Example 11, the subject matter of Example 10 optionally includes wherein the tab and threads of the threaded rod together create a ratcheting interface.

In Example 12, the subject matter of any one or more of Examples 6-11 optionally include wherein the first handle further comprises: a leg including a shoulder connected to the first handle by a hinge and including a distal threaded portion; and an actuator configured to receive the distal threaded portion to secure the actuator to the leg, the actuator axially translatable with respect to the leg, and the actuator captivated between the shoulder of the distal threaded portion of the leg, the first feature connected to a distal portion of the actuator, the first feature and the actuator rotatable about the leg when the actuator is captivated between the shoulder and the distal threaded portion.

Example 13 is a method for repairing a midline sternotomy of a sternum including a first sternal portion and a second sternal portion, the method comprising: securing a first feature of a first handle of a reduction tool to a first reduction bore of a first plate; securing a second feature of a second handle of the reduction tool to a second reduction bore of a second plate; engaging a first lateral portion of the first sternal portion with a first bone hook of the first plate; engaging a second lateral portion of the second sternal portion with a second bone hook of the second plate; and approximating and reducing the first sternal portion and the second sternal portion by operating the reduction tool to cause the first bone hook and the second bone hook to move the first sternal portion and the second sternal portion towards each other.

In Example 14, the subject matter of Example 13 optionally includes folding the reduction tool at a hinge of the reduction tool while the reduction tool is attached to the first plate and the second plate.

In Example 15, the subject matter of any one or more of Examples 13-14 optionally include driving a first fastener through a first bore of the first plate into the first sternal portion; and driving a second fastener through a second bore of the first plate into the second sternal portion.

In Example 16, the subject matter of any one or more of Examples 13-15 optionally include driving a third fastener through a third bore of the second plate into the second sternal portion; and driving a fourth fastener of through a fourth bore of the second plate into the first sternal portion.

Example 17 is a plate for securing a first sternal portion and a second sternal portion of a separated sternum, the plate comprising: a body defining: a first fastener bore configured to receive a first fastener for securing to the first sternal portion; a second fastener bore configured to receive a second fastener for securing to the second sternal portion; and a reduction bore configured to receive a reduction tool; and a hook extending outward from the body and extending distally from the body, the first hook engageable with a lateral portion of the first sternal portion to move the first sternal portion towards the second sternal portion when the reduction tool is operated to move the body via the engagement between the reduction bore and the reduction tool.

In Example 18, the subject matter of Example 17 optionally includes wherein the hook extends outward from the body adjacent the reduction bore.

In Example 19, the subject matter of Example 18 optionally includes wherein the reduction bore is aligned with the first fastener bore, the reduction bore and the first fastener bore configured to be positioned on a same side of a midline resection and configured to be positioned on an opposite side of the midline resection from the second fastener bore.

In Example 20, the subject matter of any one or more of Examples 18-19 optionally include wherein the plate includes a fifth fastener bore and a sixth fastener bore, the first fastener bore, the second fastener bore, the fifth fastener bore, and the sixth fastener bore arranged in a substantially rectangular configuration.

In Example 21, the apparatuses or method of any one or any combination of Examples 1-20 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A plate system for securing a first bone portion and a second bone portion of a separated bone structure, the plate system comprising:
    a first plate comprising:
        a first body defining:
            a first fastener bore configured to receive a first fastener for securing to the first bone portion;

a second fastener bore configured to receive a second fastener for securing to the second bone portion, and
a first reduction bore; and
a first hook extending from the first body, the first hook engageable with a lateral portion of the first bone portion;
a second plate comprising:
a second body defining:
a third fastener bore configured to receive a third fastener for securing to the first bone portion;
a fourth fastener bore configured to receive a fourth fastener for securing to the second bone portion, and
a second reduction bore; and
a second hook extending outward, or downward, or both, from the second body and extending distally from the second body, the second hook engageable with a lateral portion of the second bone portion opposite the first hook; and
a reduction tool including:
a first handle including a first feature that is insertable into the first reduction bore; and
a second handle including a second feature that is insertable into the second reduction bore, the reduction tool operable to bring the first feature and the second feature together to cause the first hook and the second hook to engage the lateral portion of the first bone portion and the lateral portion of the second bone portion, respectively, to reduce the first bone portion and the second bone portion.

2. The plate system of claim 1, wherein the first hook extends outward from the first body adjacent the first reduction bore and wherein the second hook extends outward from the second body adjacent the second reduction bore.

3. The plate system of claim 1, wherein the first plate includes a fifth fastener bore and a sixth fastener bore, the first fastener bore, the second fastener bore, the fifth fastener bore, and the sixth fastener bore arranged in a substantially rectangular configuration.

4. The plate system of claim 3, wherein the first reduction bore is aligned with the first fastener bore, the first reduction bore configured to be positioned on a same side of a midline resection as the first fastener bore and configured to be positioned on an opposite side of the midline resection from the second fastener bore.

5. The plate system of claim 4, wherein the first reduction bore is configured to be positioned on the opposite side of the midline resection from the second reduction bore.

6. The plate system of claim 1, wherein the first handle includes a first hinge and the second handle includes a second hinge, the handles foldable at the first hinge and the second hinge while the first feature is connected to the first reduction bore and the second feature is connected to the second reduction bore.

7. The plate system of claim 1, wherein the reduction tool includes an actuator operable to cause the first handle to move towards the second handle.

8. The plate system of claim 7, wherein the actuator is a threaded rod rotatable within the first handle and threadably engaged with the second handle such that rotation of the threaded rod causes the second handle to move towards the first handle.

9. The plate system of claim 8, wherein the first handle includes a tab including threading engageable with the threaded rod such that rotation of the threaded rod causes the first handle to move with respect to the second handle, the tab deflectable outward from the first handle to allow the first handle to be moved toward the second handle without rotation of the threaded rod, the tab configured to resist movement of the first handle away from the second handle without rotation of the threaded rod.

10. The plate system of claim 9, wherein the tab and threads of the threaded rod together create a ratcheting interface.

11. The plate system of claim 1, wherein the first handle further comprises:
a leg including a shoulder connected to the first handle by a hinge and including a distal threaded portion; and
an actuator configured to receive the distal threaded portion to secure the actuator to the leg, the actuator axially translatable with respect to the leg, and the actuator captivated between the shoulder of the distal threaded portion of the leg, the first feature connected to a distal portion of the actuator, the first feature and the actuator rotatable about the leg when the actuator is captivated between the shoulder and the distal threaded portion.

12. A method for repairing a midline sternotomy of a sternum including a first sternal portion and a second sternal portion, the method comprising:
securing a first feature of a first handle of a reduction tool to a first reduction bore of a first plate;
securing a second feature of a second handle of the reduction tool to a second reduction bore of a second plate;
engaging a first lateral portion of the first sternal portion with a first bone hook of the first plate;
engaging a second lateral portion of the second sternal portion with a second bone hook of the second plate;
approximating and reducing the first sternal portion and the second sternal portion by operating the reduction tool to cause the first bone hook and the second bone hook to move the first sternal portion and the second sternal portion towards each other;
driving a first fastener through a first bore of the first plate into the first sternal portion; and
driving a second fastener through a second bore of the first plate into the second sternal portion.

13. The method of claim 12, further comprising:
folding the reduction tool at a hinge of the reduction tool while the reduction tool is attached to the first plate and the second plate.

14. The method of claim 12, further comprising:
driving a third fastener through a third bore of the second plate into the second sternal portion; and
driving a fourth fastener through a fourth bore of the second plate into the first sternal portion.

15. A method for repairing a midline sternotomy of a sternum including a first sternal portion and a second sternal portion, the method comprising:
securing a first feature of a first handle of a reduction tool to a first reduction bore of a first plate;
securing a second feature of a second handle of the reduction tool to a second reduction bore of a second plate;
engaging a first lateral portion of the first sternal portion with a first bone hook of the first plate;
engaging a second lateral portion of the second sternal portion with a second bone hook of the second plate;
approximating and reducing the first sternal portion and the second sternal portion by operating the reduction tool to cause the first bone hook and the second bone hook to move the first sternal portion and the second sternal portion towards each other;

folding the reduction tool at a hinge of the reduction tool while the reduction tool is attached to the first plate and the second plate.

16. The method of claim 15, further comprising:

driving a first fastener through a first bore of the first plate into the first sternal portion; and driving a second fastener through a second bore of the first plate into the second sternal portion.

17. The method of claim 16, further comprising:

driving a third fastener through a third bore of the second plate into the second sternal portion; and driving a fourth fastener through a fourth bore of the second plate into the first sternal portion.

\* \* \* \* \*